US010617471B2

(12) United States Patent
Itoh et al.

(10) Patent No.: US 10,617,471 B2
(45) Date of Patent: Apr. 14, 2020

(54) LASER THERAPEUTIC DEVICE

(71) Applicants: NATIONAL UNIVERSITY CORPORATION NAGOYA UNIVERSITY, Aichi (JP); ASUKA MEDICAL INC., Kyoto (JP)

(72) Inventors: Yoshiyuki Itoh, Aichi (JP); Seiji Nakamura, Kyoto (JP); Keiichiro Yamada, Kyoto (JP)

(73) Assignees: NATIONAL UNIVERSITY CORPORATION NAGOYA UNIVERSITY, Aichi (JP); ASUKA MEDICAL INC., Kyoto (JP)

(*) Notice: Subject to any disclaimer, the term of this patent is extended or adjusted under 35 U.S.C. 154(b) by 192 days.

(21) Appl. No.: 15/109,274

(22) PCT Filed: Jun. 30, 2015

(86) PCT No.: PCT/JP2015/068887
§ 371 (c)(1),
(2) Date: Jun. 30, 2016

(87) PCT Pub. No.: WO2016/017349
PCT Pub. Date: Feb. 4, 2016

(65) Prior Publication Data
US 2017/0035511 A1 Feb. 9, 2017

(30) Foreign Application Priority Data

Jul. 28, 2014 (JP) .................................. 2014-152771

(51) Int. Cl.
A61B 1/00 (2006.01)
A61B 18/24 (2006.01)
(Continued)

(52) U.S. Cl.
CPC .......... A61B 18/24 (2013.01); A61B 1/00087 (2013.01); A61B 1/018 (2013.01);
(Continued)

(58) Field of Classification Search
CPC .... G02B 6/04; G02B 23/2469; G02B 6/0008; G02B 23/26; G02B 6/4206; G02B 6/262;
(Continued)

(56) References Cited

U.S. PATENT DOCUMENTS 4,836,189 A 6/1989 Allred, III et al.
6,673,065 B1 * 1/2004 Veligdan ................ A61B 18/20
606/13

(Continued)

FOREIGN PATENT DOCUMENTS

JP 59-137069 8/1984
JP 62-183980 8/1987
(Continued)

OTHER PUBLICATIONS

International Search Report dated Sep. 1, 2015 in International (PCT) Application No. PCT/JP2015/068887.
(Continued)

Primary Examiner — Alexandra L Newton
(74) Attorney, Agent, or Firm — Wenderoth, Lind & Ponack, L.L.P.

(57) ABSTRACT

A laser therapeutic device for a laser endoscope capable of relatively reducing the diameter of the endoscope while being capable of emitting a laser beam of a uniform intensity over a wide area is provided. An optical guide element (a square-shaped rod lens 15, a guide tube 2b) having a quadrangular cross section and guiding a therapeutic laser beam emitted from the tip of an optical fiber toward the tip side of a probe is used. On the tip side of a probe tube 2 being a barrel, using clearances C1 to C4 formed between (Continued)

the optical guide element and the inner circumferential surface of the probe tube, a camera unit 11 as imaging means and white-color LED units 12 and an ultraviolet LED unit 13 as illumination means are arranged.

18 Claims, 11 Drawing Sheets

(51) Int. Cl.
*A61B 1/018* (2006.01)
*A61B 1/05* (2006.01)
*A61B 1/06* (2006.01)
*A61B 18/00* (2006.01)
*A61B 90/30* (2016.01)
*A61B 18/22* (2006.01)

(52) U.S. Cl.
CPC ............ *A61B 1/051* (2013.01); *A61B 1/0684* (2013.01); *A61B 2018/00702* (2013.01); *A61B 2018/00791* (2013.01); *A61B 2018/00982* (2013.01); *A61B 2018/2205* (2013.01); *A61B 2018/2266* (2013.01); *A61B 2090/309* (2016.02)

(58) Field of Classification Search
CPC ... G02B 6/4202; A61B 1/00165; A61B 1/002; A61B 1/063; A61B 1/0646; A61B 1/00181; A61B 1/00193; A61B 1/05; A61B 1/051; A61B 1/043; A61B 1/303; A61B 1/0683
See application file for complete search history.

(56) References Cited

U.S. PATENT DOCUMENTS

| | | | |
|---|---|---|---|
| 2002/0035360 A1* | 3/2002 | Connors | A61B 18/203 606/9 |
| 2009/0326523 A1* | 12/2009 | Lazarev | A61B 18/203 606/9 |
| 2012/0029279 A1 | 2/2012 | Kucklick | |
| 2012/0029280 A1 | 2/2012 | Kucklick | |
| 2012/0029289 A1* | 2/2012 | Kucklick | A61B 1/00089 600/156 |
| 2012/0059222 A1* | 3/2012 | Yoshida | A61B 1/00091 600/157 |
| 2012/0249764 A1* | 10/2012 | Kuon | A61B 1/05 348/67 |
| 2014/0316199 A1* | 10/2014 | Kucklick | A61B 1/317 600/109 |
| 2015/0005575 A1* | 1/2015 | Kobayashi | A61B 1/00009 600/103 |

FOREIGN PATENT DOCUMENTS

| | | | |
|---|---|---|---|
| JP | 2001292956 A | * | 10/2001 |
| JP | 2003-135483 | | 5/2003 |
| JP | 2013-537446 | | 10/2013 |
| JP | 2015-9031 | | 1/2015 |

OTHER PUBLICATIONS

English translation of International Preliminary Report on Patentability and Written Opinion of the International Searching Authority dated Jan. 31, 2017 in corresponding International (PCT) Application No. PCT/JP2015/068887.

* cited by examiner

<With square-shaped rod lens>

<With bare fiber>

LASER THERAPEUTIC DEVICE

TECHNICAL FIELD

The present invention relates to a laser therapeutic device that can be installed in an endoscope, and particularly to a laser therapeutic device that enables effective hyperthermia by uniformly irradiating a wide area through use of an optical guide element having a quadrangular cross section.

BACKGROUND ART

An endoscope is a medical device that is mainly intended to observe inside the human body. An optical system is installed inside a barrel of the endoscope, and a tip of the barrel is inserted into the human body to display an image inside the human body on a monitor. In recent years, a laser endoscope in which a laser therapeutic device is installed in the endoscope has particularly attracted attention as a new cancer treatment. In the treatment, cancer is normally removed roughly by a conventional endoscopic surgery and remaining cancer cells are then completely extinguished by irradiating the removed area with a laser beam of the laser endoscope.

Further, in the case where a tumor is relatively small and not deeply invading into the tissue, it has also been attempted without carrying out an endoscopic surgery to destroy cancer cells solely by hyperthermia with the laser endoscope. The hyperthermia (thermal therapy for cancers) is a treatment which heats a tumor locally at a temperature of 42° C. or more for 30 to 60 minutes. The hyperthermia not only kills cancer cells, it is also expected to improve by heating the immune function of normal cells as well as the effect of radiation and chemotherapy.

In endoscopic operations, depending on their method and purpose, a rigid endoscope having a rigid bar-like barrel or a flexible endoscope having a barrel made of a flexible tube is selectively used. Though the laser therapeutic device of the present invention is mainly installed in a rigid endoscope, miniaturization thereof enables itself to be installed also in a flexible endoscope.

As for types of endoscope, there are an optical type in which a plurality of lenses is stored in the barrel and an electronic type in which a camera unit of a CCD image sensor is arranged at the tip of the barrel. An illumination unit (an external light introduction type or an LED emission type) capable of emitting intensive light is provided at the tip of the barrel. There is also an endoscope provided with an operation tool for surgery, and for example, Patent Literature 1 (U.S. Pat. No. 4,836,189) is known to disclose a hysteroscope including a laser scalpel.

CITATION LIST

Patent Literature

Patent Literature 1: U.S. Pat. No. 4,836,189

SUMMARY OF THE INVENTION

Technical Problems

Though each thickness (diameter) of the endoscopes varies from large size to small size depending on their type, generally, the diameter tends to be reduced in order to alleviate a burden on patients. The conventional laser endoscope generally uses a bare fiber (bare core optical fiber) for guiding a laser beam.

As the bare fiber uses an optical fiber having a circular cross section, the beam profile in contactless radiation forms a bell shape in which the heights of the shape in cross section are formed lowering from the highest center part to the periphery. Accordingly, the region effective for the laser treatment is limited to the central portion of the beam profile, and the available region relative to the whole cross section of the fiber is small.

Further, the irradiation region with a laser endoscope using the bare fiber is circular similarly to the cross section of the fiber. Therefore, when a wide area is to be irradiated with laser by shifting the irradiation region, the irradiation regions do not evenly overlap. As a result, while the intensity tends to be insufficient at the peripheral portion of the irradiation region, the intensity is conversely excessively strong at the central portion of the irradiation region. Accordingly, in performing hyperthermia, it is difficult to uniformly irradiate a wide area with laser efficiently in a short period. As a result, a burden is put on patients or the treatment effect fails to be fully achieved.

In order to emit a laser beam of a uniform intensity over a wide area, it is necessary to increase the diameter of the optical fiber. However, this invites an increase in the diameter of the whole laser endoscope, posing problems of limitation on the sites where the endoscope can be used, a greater burden on patients, and poor operability.

Accordingly, an object of the present invention is to provide a laser therapeutic device for a laser endoscope capable of relatively reducing the diameter of the endoscope while being capable of emitting a laser beam of a uniform intensity over a wide area.

Solution to Problems

In order to solve the above problem, the present invention provides a laser therapeutic device including: an optical fiber for guiding a therapeutic laser beam; a probe tube being a barrel of an endoscope to which a tip of the optical fiber is connected; an optical guide element having a quadrangular cross section arranged in the probe tube for guiding a laser beam emitted from the tip of the optical fiber toward a tip side of the probe tube; and imaging means and illumination means both arranged in clearances formed between sides of the optical guide element and an inner circumferential surface of the probe tube.

Advantageous Effects of Invention

The laser therapeutic device of the present invention uses an optical guide element having a quadrangular cross section and guiding a laser beam emitted from the tip of an optical fiber toward the tip side of the probe tube. Therefore, a laser beam of a so-called top-hat type having a uniform intensity can be emitted over a wide area. Further, the imaging means and the illumination means are both arranged without uselessly utilizing the clearances formed between the optical guide element having a quadrangular cross section and the inner circumferential surface of the probe tube. Accordingly, the diameter of the probe tube being the barrel when installed in an endoscope can be reduced. This realizes an effective laser treatment (hyperthermia) by uniform radiation over a wide area, with smaller burden on the patients and excellent operability.

BRIEF DESCRIPTION OF THE DRAWINGS

FIG. 8Bb is a conceptual diagram of the beam profile of a laser beam with a bare fiber.

DESCRIPTION OF EMBODIMENTS

Figure 1:
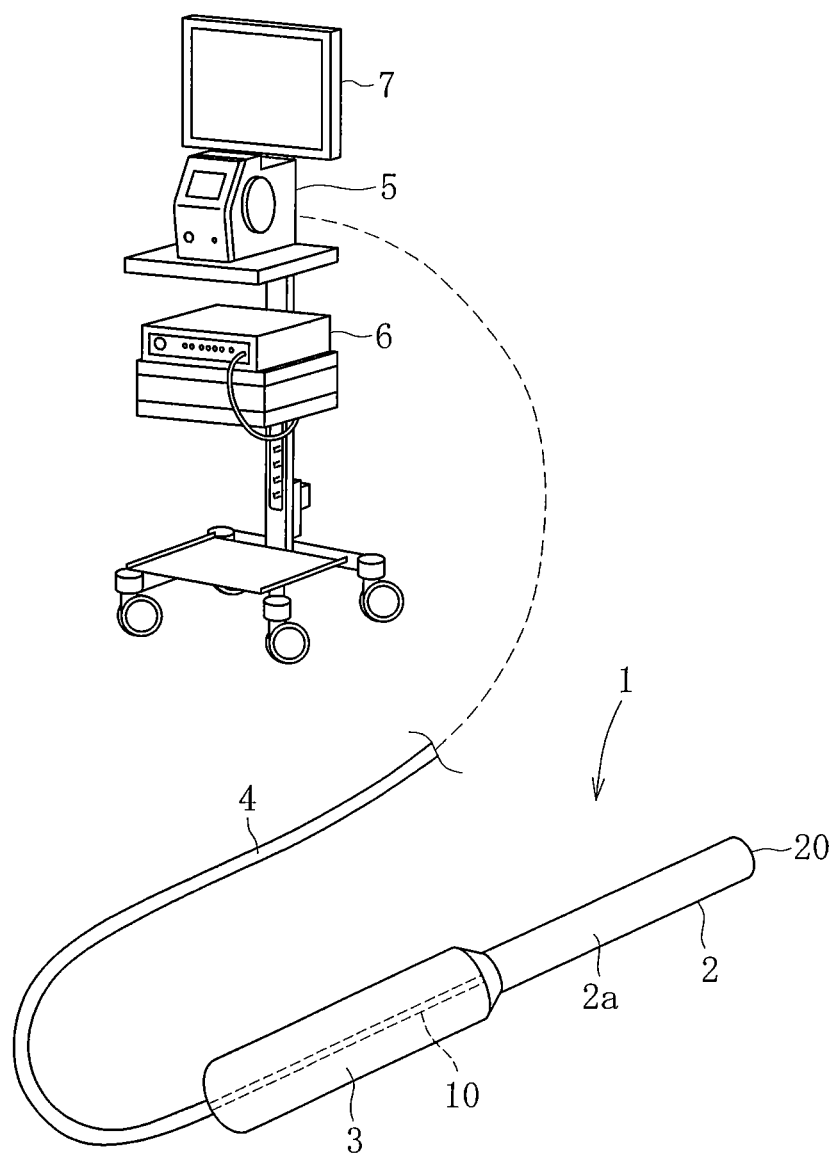
FIG. 1 is an overall schematic diagram of an endoscope laser system for treating cervical cancer using a laser therapeutic device according to an embodiment of the present invention.

In the following, with reference to the drawings, a description will be given of a laser therapeutic device according to an embodiment of the present invention. FIG. 1 is an overall schematic diagram of an endoscope laser system for treating uterine cervix cancer using a laser therapeutic device 1. The endoscope used in the system is a rigid endoscope, which can be used not only as the uterine cervix cancer endoscope but also as a laparoscope, a thoracoscope, a cystoscope and the like.

The laser therapeutic device 1 includes a probe tube 2 being a barrel structured by a cylindrical body 2a having a circular cross section. A handpiece 3 is attached to the proximal end of the probe tube 2.

To the proximal end of the handpiece 3, a cable 4 storing an optical fiber 10 and electrical lines (not shown) is connected. Via the cable 4, the laser therapeutic device 1 is connected to a laser oscillator 5 and a controller 6. The controller 6 outputs an image of a camera unit 11, which will be described later, on a liquid crystal monitor 7.

Figure 2A:
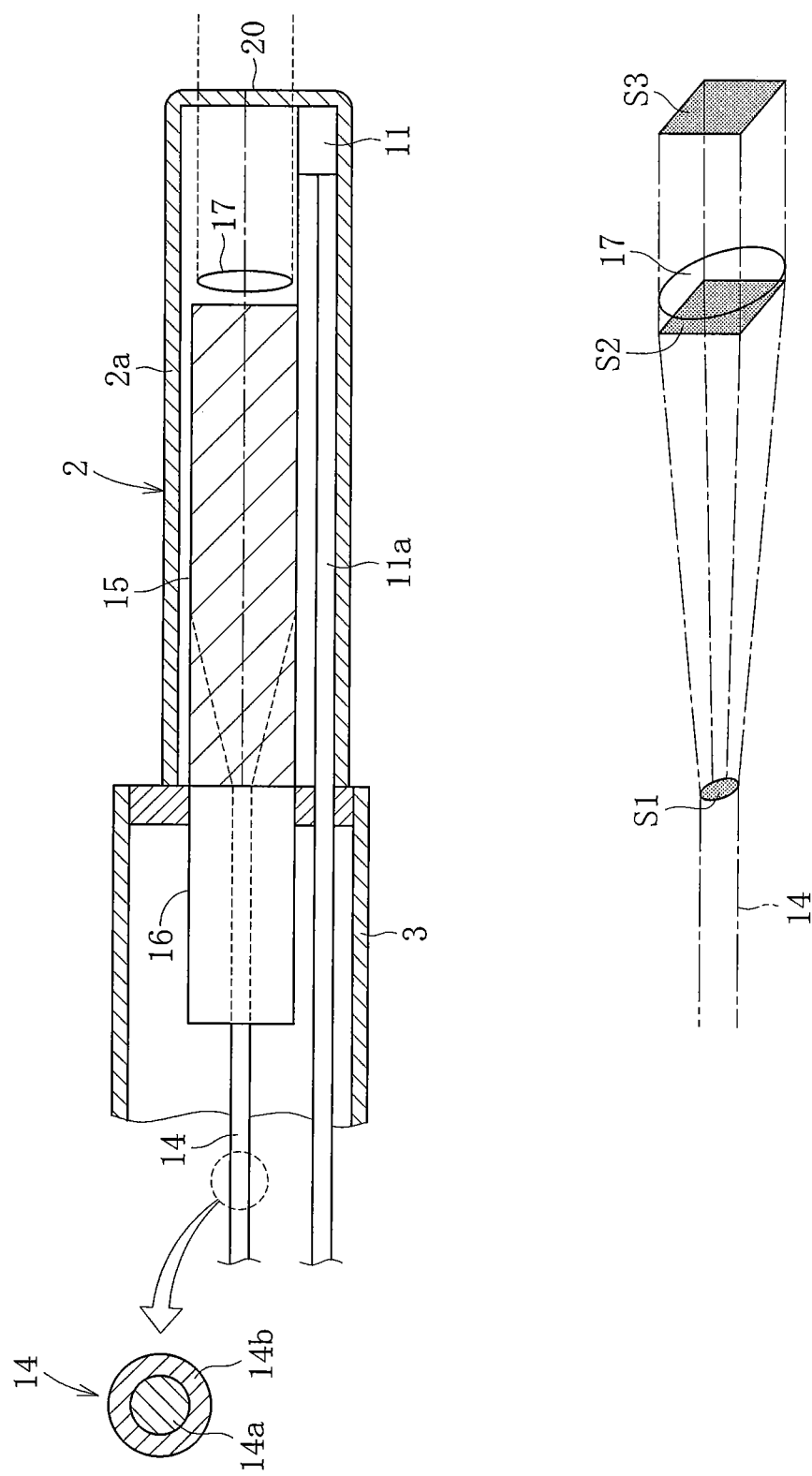
FIG. 2A is a vertical cross-sectional view of the tip portion of a probe tube of the laser therapeutic device.

The cylindrical body 2a structuring the probe tube 2 is cylindrically shaped to have a diameter of, for example, about 30 mm. At a substantially central position inside the cylindrical body 2a, as shown in FIG. 2A, a square-shaped rod lens 15 as an optical guide element is arranged. The tip of the optical fiber 10 is connected to the proximal end of the square-shaped rod lens 15 via a connector 16. Note that, though the cross section of the square-shaped rod lens 15 is square, it may be rectangle.

An optical fiber 14 is a bare fiber that is available at low costs, and has a core 14a having a circular cross section and a clad 14b covering the outer circumference of the core 14a. The end surface of the core 14a is connected to the proximal end surface of the square-shaped rod lens 15.

The tip portion of the cylindrical body 2a is a transparent laser emission unit 20. The tip portion of the square-shaped rod lens 15 extends to the position near the laser emission unit 20.

A converging lens 17 is arranged in front of the tip portion of the square-shaped rod lens 15. The converging lens 17 enhances the convergence of a quadrangular laser beam emitted from the tip portion of the square-shaped rod lens 15. Note that, it is also possible to eliminate the converging lens 17 by arranging the tip portion of the square-shaped rod lens 15 close to the laser emission unit 20.

In the present embodiment, as will be described later, imaging means and illumination means are arranged in a ship-bottom shaped clearance formed between the square-shaped rod lens 15 and the probe tube 2a.

The laser therapeutic device 1 is structured as described above, and as shown by the lower illustration in FIG. 2A, a circular laser beam S1 (for example, of a diameter 600 μm) emitted from the end of the optical fiber 14 enters the square-shaped rod lens 15. The circular laser beam S1 is shaped into a quadrangular shape while passing through the square-shaped rod lens 15, and emitted as a quadrangular laser beam S2 from the tip of the square-shaped rod lens 15.

Thereafter, the quadrangular laser beam S2 further passes through the converging lens 17, and converges as a quadrangular laser beam S3 (for example, of 20 mm square) in the laser emission unit 20. With the quadrangular laser beam S3, a laser treatment such as hyperthermia can be performed.

Next, with reference to FIGS. 3A to 3C, a variation of the present invention will be described. In the variation, in place of the above-described square-shaped rod lens 15, a quadrangular optical fiber 10 and a guide tube 2b as an optical guide element having a quadrangular cross section are used. The guide tube 2b is structured by a square tube whose inner surface is a reflective surface reflecting the laser beam.

Figure 3A:
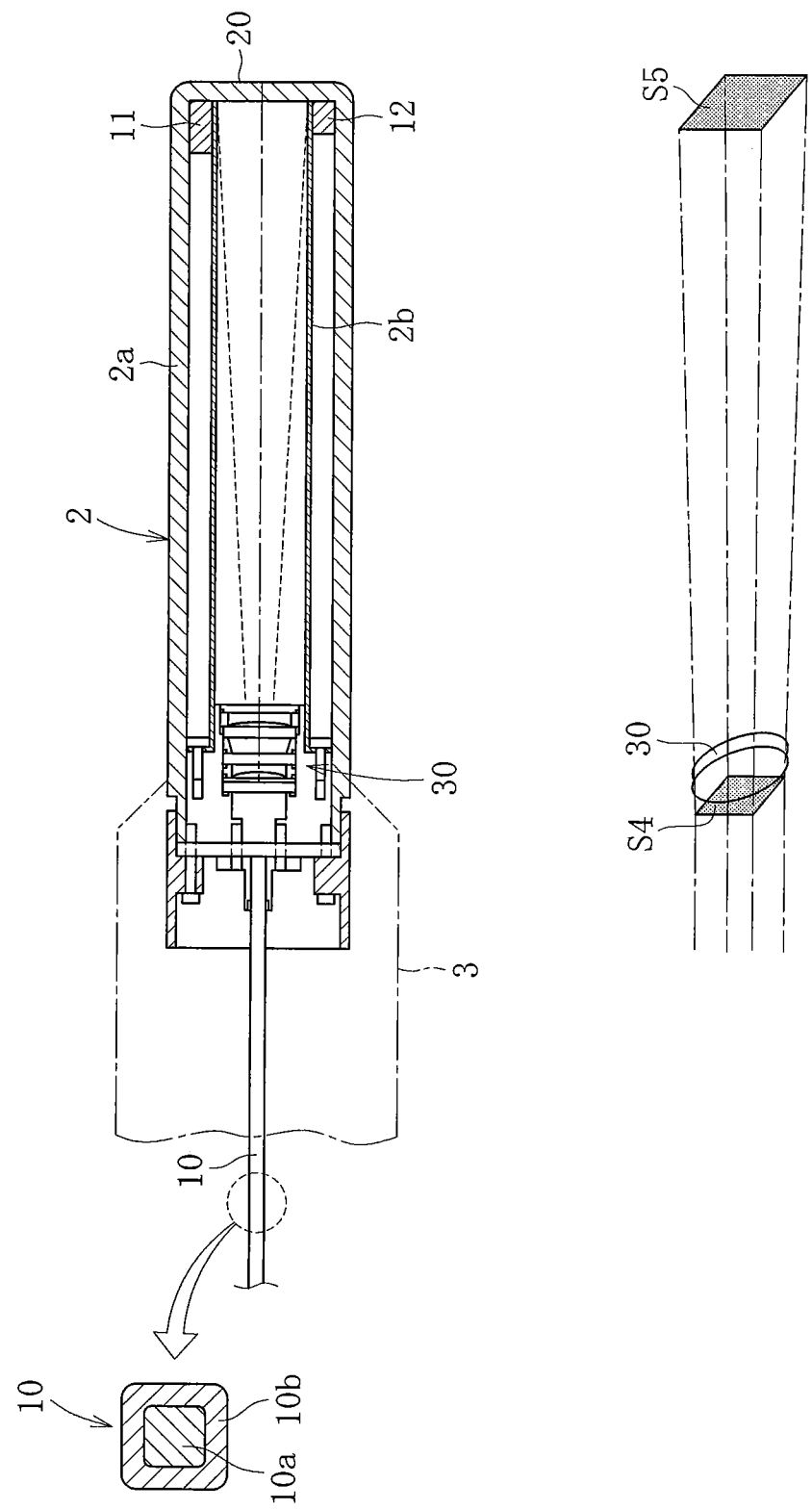
FIG. 3A is a vertical cross-sectional view of the tip portion of a probe tube of a laser therapeutic device according to a variation.

Specifically, as shown in FIG. 3A, the tip of the optical fiber 10 is connected to an optical system 30 in the handpiece 3. The optical fiber 10 has a core 10a having a quadrangular (square) cross section, and a clad 10b covering the outer circumference of the core 10a. The end surface of the core 10a is connected to the optical system 30.

The emission side on the right side of the optical system 30 is connected to the guide tube 2b having a quadrangular (square) cross section and coaxially arranged in the cylindrical body 2a. The guide tube 2b extends to the tip portion of the cylindrical body 2a. The tip portion of the cylindrical body 2a is connected to the transparent laser emission unit 20.

Figure 3B:
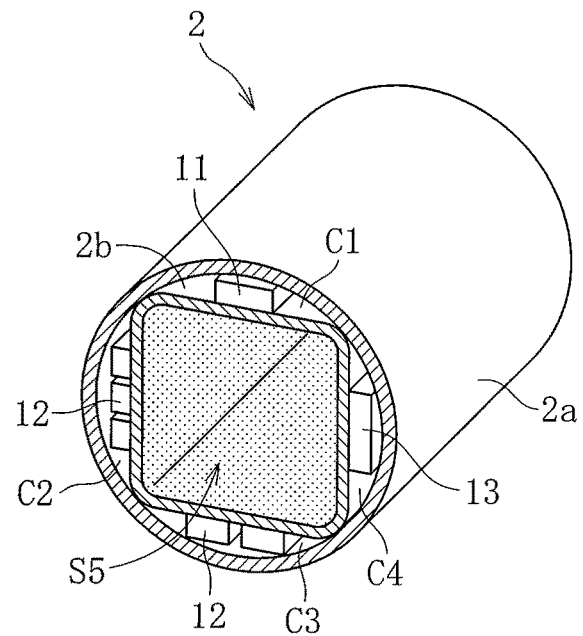
FIG. 3B is an internal perspective view of the tip portion of the probe tube of the laser therapeutic device according to the variation.

As shown in FIG. 3B, the four corners of the guide tube 2b are in contact with the inner circumferential surface of the cylindrical body 2a having a circular cross section. Accordingly, between the linear sides of the guide tube 2b and the inner circumferential surface of the cylindrical body 2a, ship-bottom shaped four clearances (a first clearance C1 to a fourth clearance C4) are formed.

In the variation, as shown in the lower illustration in FIG. 3A, a quadrangular laser beam S4 (for example, of a diameter 600 µm) emitted from the end of the optical fiber 10 enters the optical system 30. The quadrangular laser beam S4 output from the optical system 30 is enlarged maintaining the quadrangular shape while passing through the guide tube 2b, and emitted as a quadrangular laser beam S5 of a large area (for example, 20 mm square) from the tip of the guide tube 2b. With the quadrangular laser beam S5, a laser treatment such as hyperthermia can be performed.

In the embodiment and the variation of the present invention, the ship-bottom shaped clearances formed around the square-shaped rod lens 15 as the optical guide element having a quadrangular cross section and the cylindrical body 2a are effectively used as the spaces for arranging the imaging means and the illumination means.

Figure 2B:
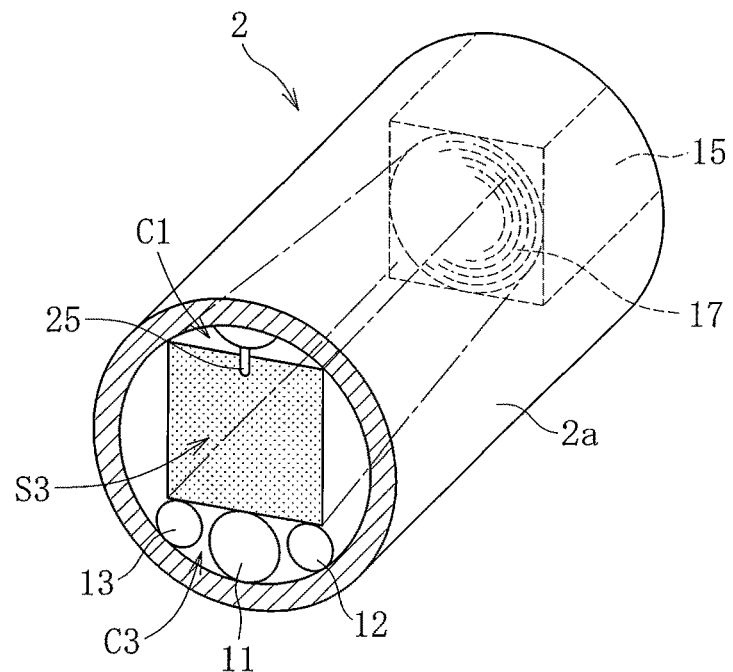
FIG. 2B is an internal perspective view of the tip portion of the probe tube of the laser therapeutic device.
Figure 2C:
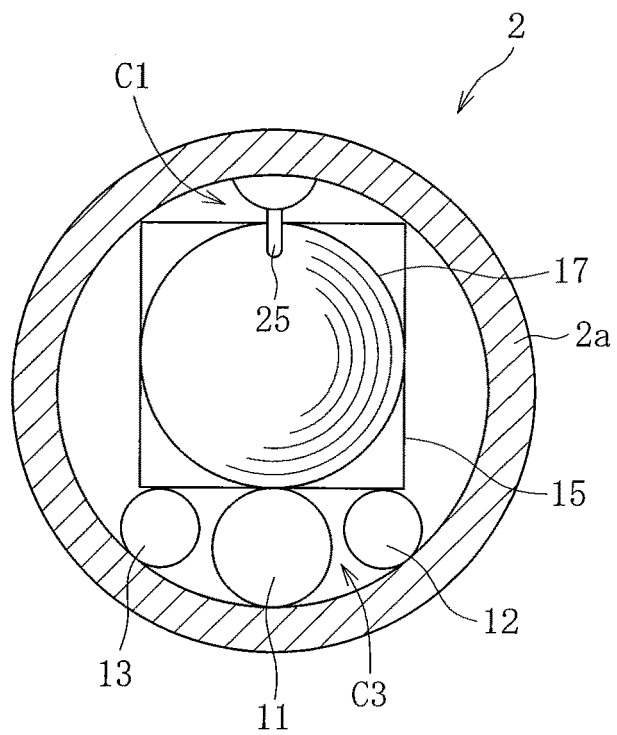
FIG. 2C is a horizontal cross-sectional view of the tip portion of the probe tube of the laser therapeutic device.

That is, in the embodiment, as shown in FIGS. 2B and 2C, in the ship-bottom shaped clearance C1 formed on the upper side of the square-shaped rod lens 15, a temperature sensor unit 25 is arranged. Further, in the ship-bottom shaped clearance C3 formed on the lower side of the square-shaped rod lens 15, the camera unit 11 using a CCD image sensor as the imaging means and white-color LED units 12 and an ultraviolet LED unit 13 as the illumination means are arranged.

The ultraviolet LED unit 13 is used for discerning the difference between normal tissue and abnormal tissue, based on the difference in intensity of autofluorescence emitted by the tissue when the tissue is irradiated with ultraviolet light. The wirings for supplying power to the camera unit 11 and others extend to the handpiece 3 through the clearances C1 and C3 around the square-shaped rod lens 15 (in FIG. 2A, only a wiring 11a of the camera unit 11 is shown).

Further, in the variation shown in FIG. 3B, all the four ship-bottom shaped clearances C1 to C4 are used to dispersely arrange the imaging means and the illumination means. That is, the camera unit 11 using the CCD image sensor as the imaging means is arranged in the first clearance C1, and three white-color LED units 12 as the illumination means are arranged in the second clearance C2.

Further, two white-color LED units 12 as the illumination means are arranged in the third clearance C3 opposing to the camera unit 11 having the optical fiber 10 interposed therebetween. One ultraviolet LED unit 13 as the illumination means is arranged in the fourth clearance C4. Note that, it goes without saying that the number of the white-color and ultraviolet LEDs can be changed as appropriate in accordance with the size of the clearances C2 to C4 and the type of the LEDs.

Note that, as known in connection with the conventional endoscope, a cleaning nozzle unit may be arranged adjacent to the camera unit 11. By injecting saline from the cleaning nozzle unit to the camera unit 11, blood and the like adhered to the camera unit 11 can be removed.

Figure 4A:
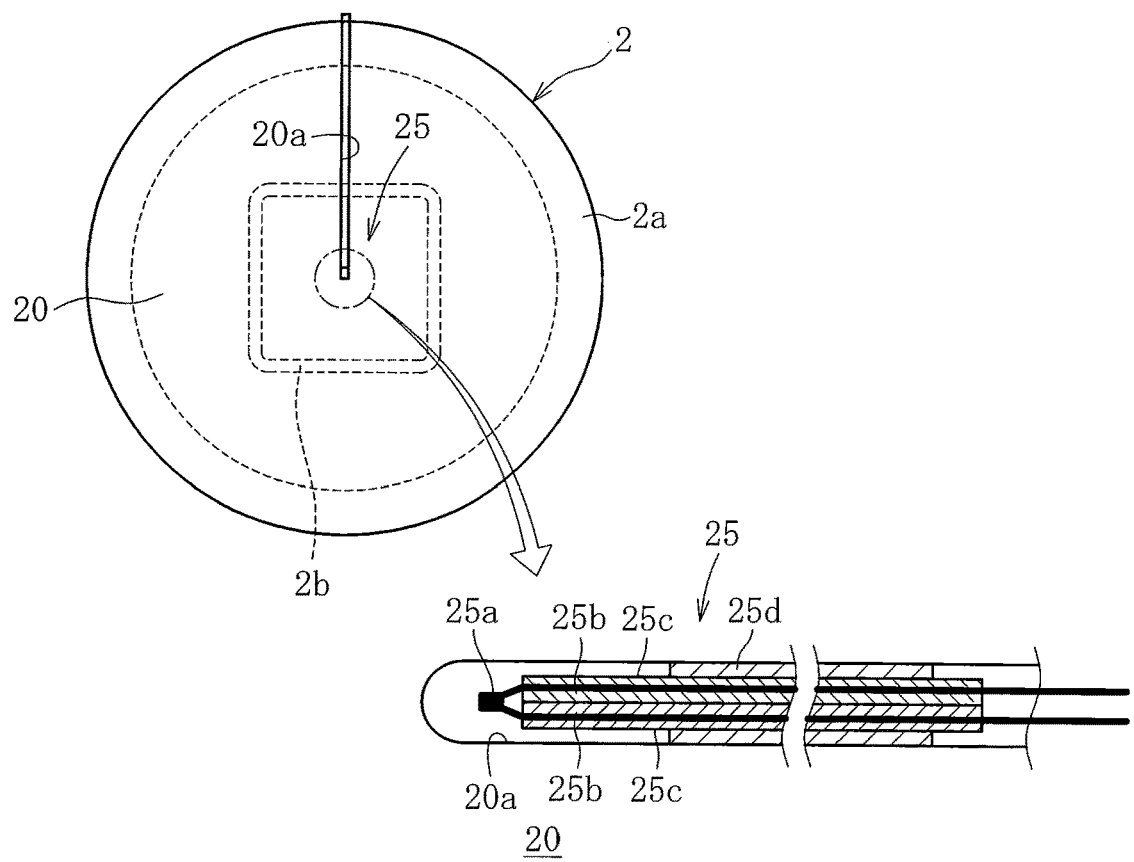
FIG. 4A is a diagram showing the tip surface of a temperature sensor arranged at the tip portion of the probe tube of the laser therapeutic device.
Figure 4B:
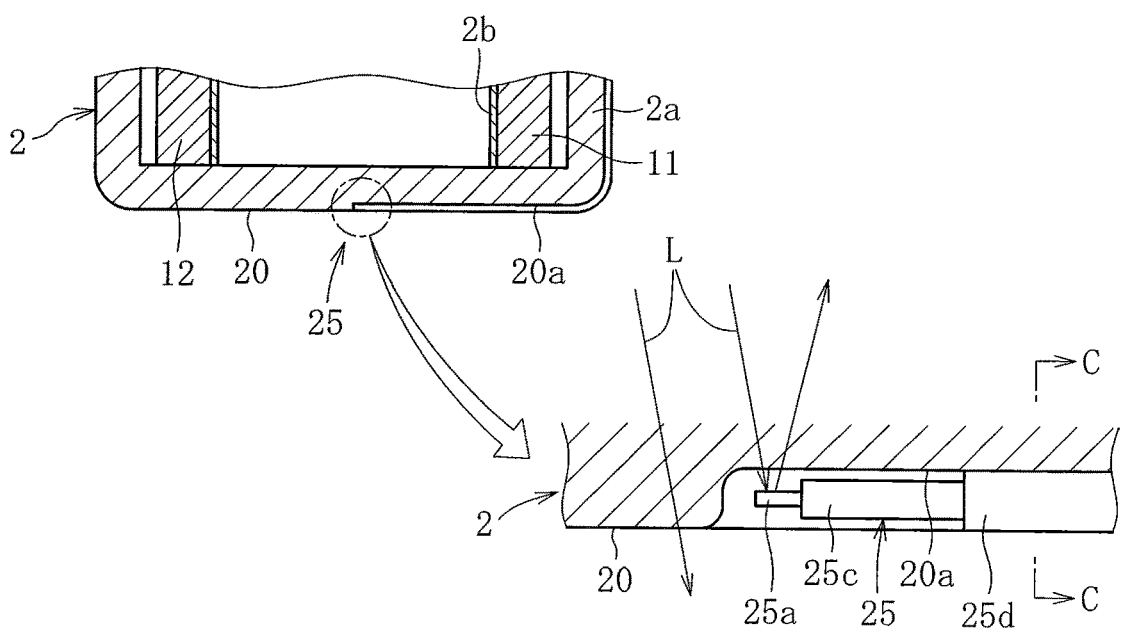
FIG. 4B is a cross-sectional view of the temperature sensor shown in FIG. 4A.
Figure 4C:
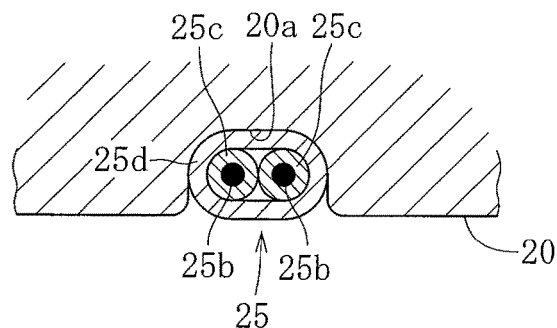
FIG. 4C is a cross-sectional view taken along line C-C in FIG. 4B.

As shown in FIGS. 4A to 4C in detail, the above-described temperature sensor unit 25 is arranged at the laser emission unit 20 at the tip of the cylindrical body 2a. The temperature sensor unit 25 is structured with a coated thermocouple in which a measurement point 25a is exposed. In the drawings, 25b denotes a thermocouple wire, 25c denotes a thermocouple wire coating insulator, and 25d denotes a sheath insulator.

The temperature sensor unit 25 is stored in a radial groove 20a formed from the central portion toward the periphery of the laser emission unit 20. The coated thermocouple of the temperature sensor unit 25 may be of an extremely thin size, which is immediately available from a plurality of manufacturers, even the one having a major axis of 0.5 mm or less. The coated thermocouple is desirably entirely gold plated, so as not to be affected by the laser beam L.

The measurement point 25a is provided at the tip of the temperature sensor unit 25, and the measurement point 25a is positioned at the center of the laser emission unit 20. In connection with the temperature sensor unit 25, it is also possible that the radial groove 20a is not formed at the laser emission unit 20 and the temperature sensor unit 25 may be exposed at the laser emission unit 20 by being bonded by an adhesive agent or the like. Alternatively, only the measurement point 25a may be exposed at the laser emission unit 20 and the rest of the temperature sensor unit 25 may be embedded in the laser emission unit 20.

In hyperthermia, a depth of about 5 to 10 mm from the surface of the tissue is heated to 42° C. or more. Accordingly, in order to surely attain this temperature, the wavelength and intensity of the laser beam are adjusted based on the output of the temperature sensor unit 25.

Figure 5:
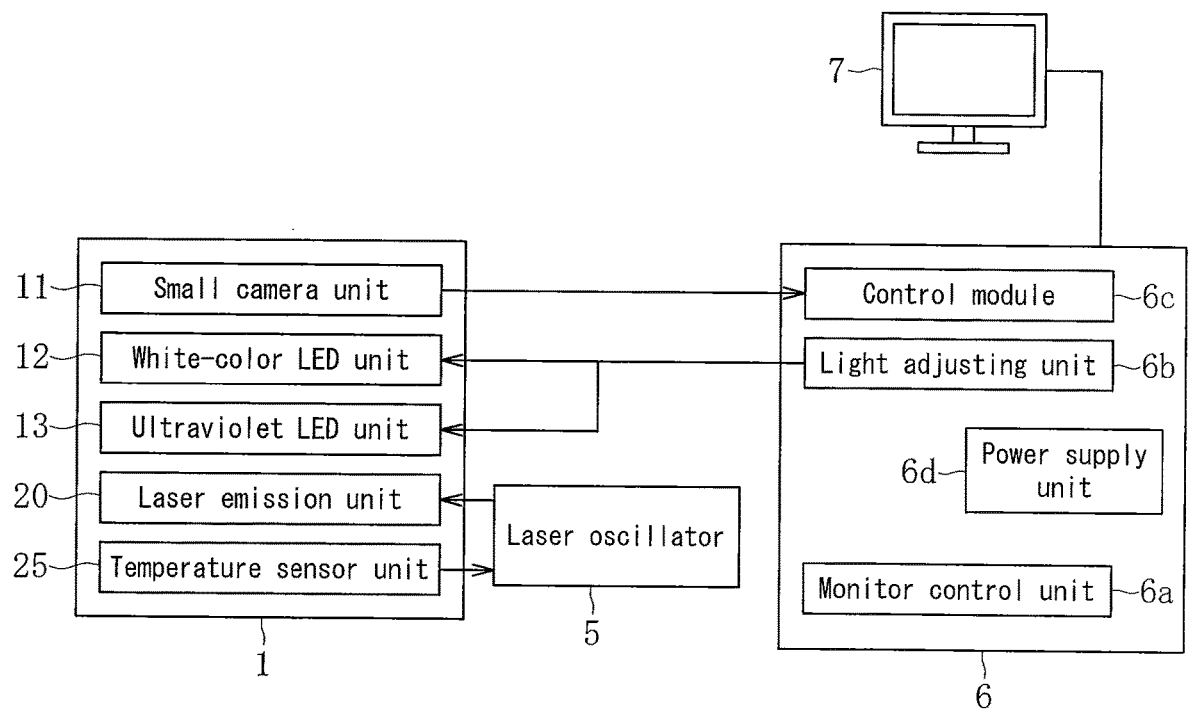
FIG. 5 is a block diagram of an endoscope laser system.

FIG. 5 is a block diagram of the endoscope laser system for treating uterine cervix cancer. The small camera unit 11, the white-color LED units 12, and the ultraviolet LED unit 13 are controlled by the controller 6. The controller 6 includes a monitor control unit 6a, a light adjusting unit 6b, a control module 6c, and a power supply unit 6d. The output of the temperature sensor unit 25 is fed back to the laser oscillator 5, whereby the wavelength and intensity of the laser beam are adjusted.

Figure 3C:
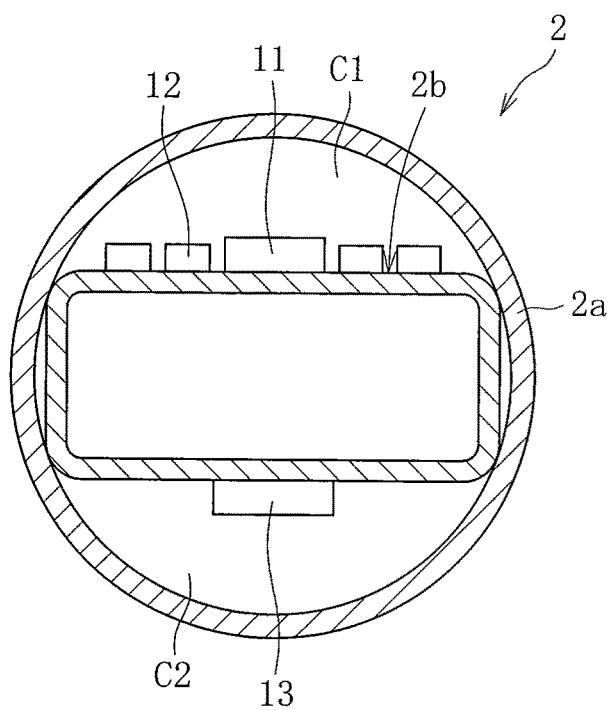
FIG. 3C is a horizontal cross-sectional view of the tip portion of a probe tube of a laser therapeutic device according to another variation.

The cross-sectional shape of the optical fiber and that of the guide tube are not necessarily square as shown in FIG. 3B, and may be rectangular as shown in FIG. 3C. In this case, since relatively great first clearance C1 and second clearance C2 are respectively formed above and beneath the guide tube 2b, for example the camera unit 11 and the white-color LED units 12 are arranged in the first clearance C1, and the ultraviolet LED unit 13 is arranged in the second clearance C2.

Figure 6A:
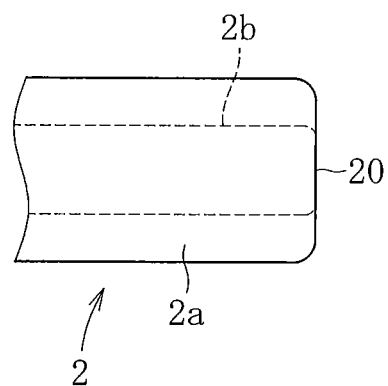
FIG. 6A is a side view of the tip portion of the probe tube of the laser therapeutic device, being a side view of the type in which a laser emission unit is not projected.
Figure 6B:
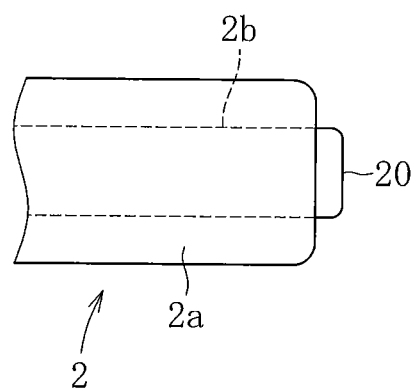
FIG. 6B is a side view of the tip portion of the probe tube of the laser therapeutic device, being a side view of the type in which the laser emission unit is projected.

The laser emission unit 20 at the tip of the laser therapeutic device 1 may be arranged on the same plane as the tip surface of the probe tube 2 as shown in FIG. 6A, or may be arranged as being slightly projected from the tip surface of the probe tube 2 as shown in FIG. 6B. By arranging the laser emission unit 20 as being projected as shown in FIG. 6B, the laser emission unit 20 can be easily intimately attached to a tumor, and the laser beam can be effectively emitted easily.

Figure 7:
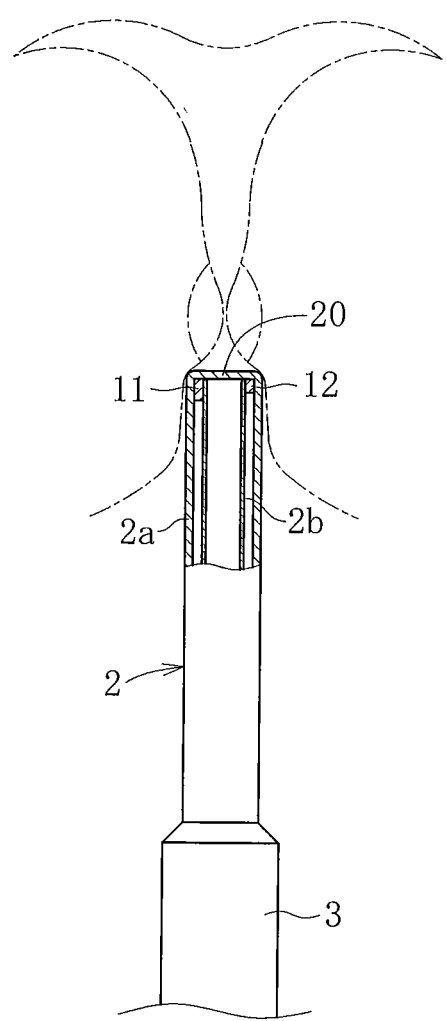
FIG. 7 is a diagram showing an example of use as a laser endoscope for uterine cervix cancer.

FIG. 7 shows an example of use of a endoscope for uterine cervix cancer in which the laser therapeutic device 1 according to the variation of the present invention is installed. The laser beam emitted from the laser emission unit 20 is projected over a wide quadrangular area, and as will be described later, has a laser profile of a top-hat type and of a uniform intensity. Therefore, the surface of a tumor can be heated over a wide area to a uniform temperature. Accordingly, for example in connection with uterine cervix cancer or the like, the uterine cervix cancer endoscope can be used to cover the entire tumor under an irradiation range, and completely destroy the cancer cells by one-time radiation. Note that, the laser therapeutic device 1 using the square-shaped rod lens 15 according to the embodiment of the present invention can be used in an identical manner, and similar operation and effect can be achieved.

Figure 8A:
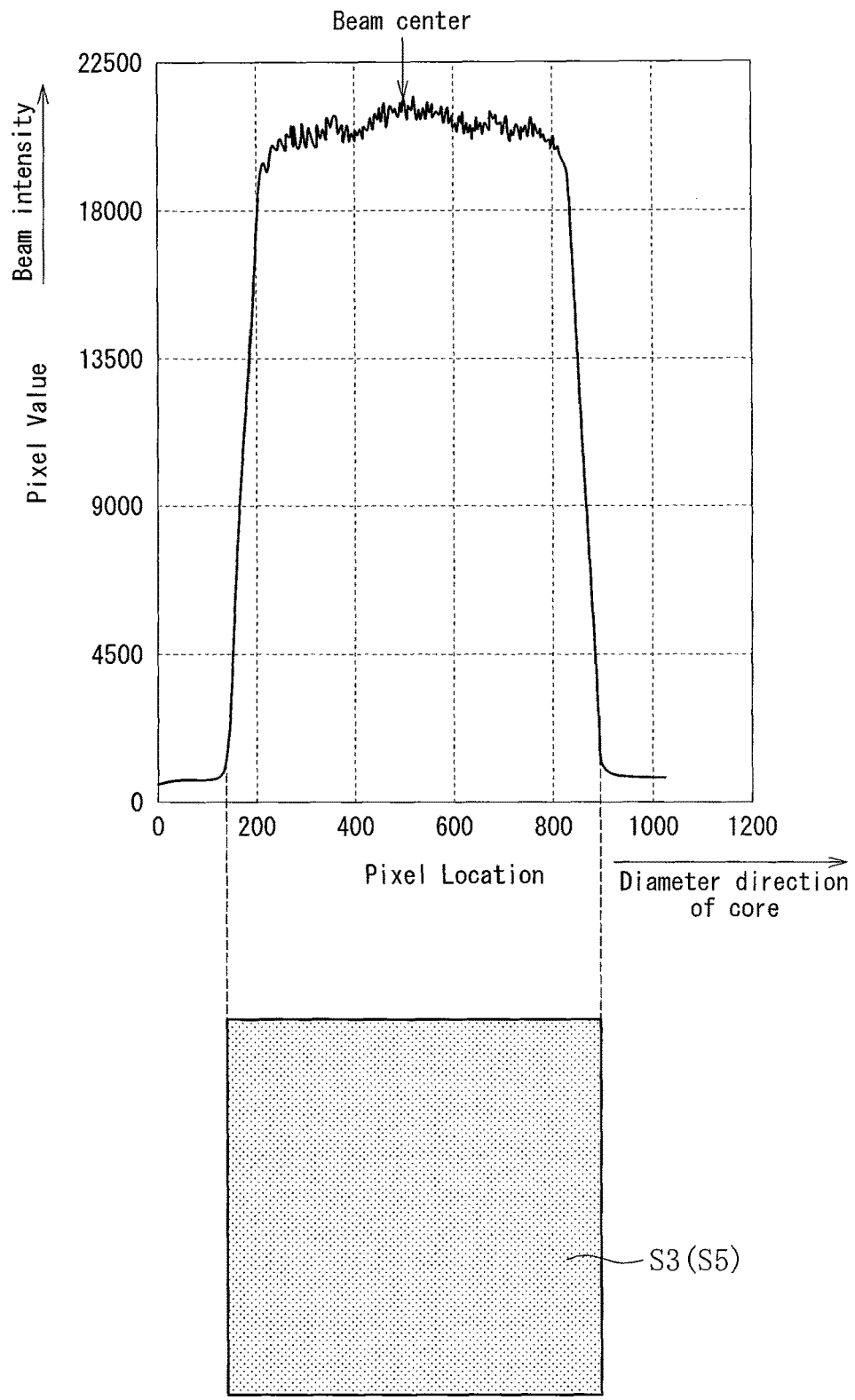
FIG. 8A is a diagram showing the beam profile of a quadrangular laser beam.

Irrespective of whether the cross-sectional shape of the square-shaped rod lens 15 as the optical guide elements and the cylindrical body 2a is square or rectangular, the quadrangular laser beams S3 and S5 emitted from the optical guide element each have a so-called top-hat type uniform beam profile as shown in FIG. 8A. While the output of the laser beam may be for example about 5 W in normal hyperthermia, depending on the content of the treatment, the output may be as low as several hundred mW.

Figure 8B:
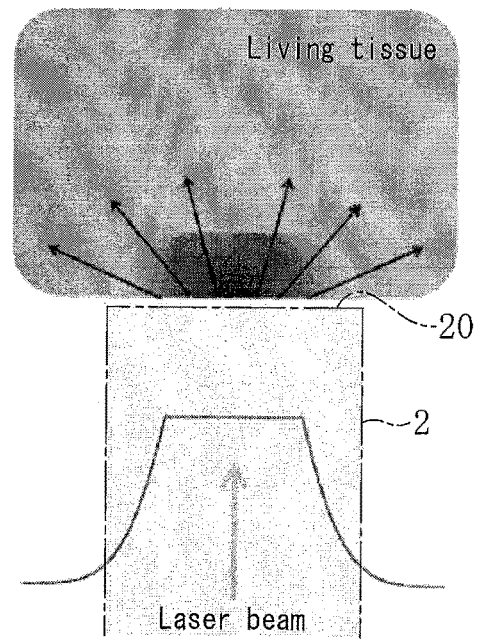
FIG. 8Ba is a conceptual diagram of the beam profile of a laser beam with a quadrangular fiber.
Figure 8B:
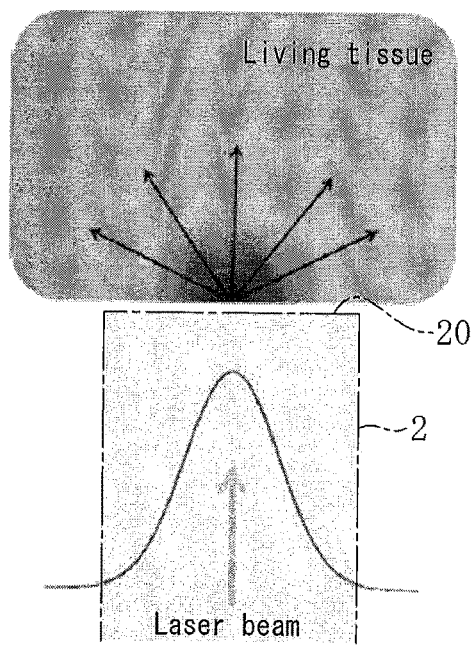

FIGS. 8Ba and 8Bb are conceptual diagrams comparing between the square-shaped rod lens and the bare fiber (bare core optical fiber). As shown, the square-shaped rod lens is capable of emitting a laser beam of a constant intensity over a wide area as compared to the bare fiber. Accordingly, the treatment effect of hyperthermia can be improved. Note that, when the quadrangular optical fiber 10 and the guide tube 2b are used also, a laser beam of a top-hat type and of a uniform intensity similarly to that shown in FIG. 8Ba can be obtained.

In the foregoing, while one embodiment of the present invention has been described, the present invention is not limited to the above embodiment, and can be modified in various manners. For example, while the illumination units of the white-color LED units 12 and the ultraviolet LED unit 13 are exemplarily shown, the present invention is not limited to such LEDs and includes other illumination unit. For example, other illumination unit may be of an external light introduction type in which an illumination purpose external laser beam is introduced by an optical fiber.

REFERENCE SIGNS LIST

1: laser therapeutic device
2: probe tube
3: handpiece
4: cable
5: laser oscillator
6: controller
7: liquid crystal monitor
10, 14: optical fiber
11: camera unit
12: white-color LED unit
13: ultraviolet LED unit
20: laser emission unit
25: temperature sensor unit
30: optical system
C1 to C4: ship-bottom shaped clearance

The invention claimed is:
1. A laser therapeutic device comprising:
an optical fiber for guiding a therapeutic laser beam;
a hollow probe tube being a barrel of an endoscope to which a tip of the optical fiber is connected, the hollow probe tube having an inner circumferential surface defining a cavity;
an optical guide element having a quadrangular cross section arranged in the cavity of the hollow probe tube for guiding a laser beam emitted from the tip of the optical fiber toward a tip side of the hollow probe tube; and
imaging means and illumination means both arranged in the cavity of the hollow probe tube within clearances formed between sides of the optical guide element and the inner circumferential surface of the hollow probe tube,
wherein the clearances are separated from each other by corners of the optical guide element contacting the inner circumferential surface of the hollow probe tube.

2. The laser therapeutic device according to claim 1, wherein
the optical fiber is a bare fiber having a circular cross section, and the optical guide element is a square-shaped rod lens.

3. The laser therapeutic device according to claim 2, further comprising
a converging lens arranged at a tip of the square-shaped rod lens to enhance convergence of the laser beam emitted from the tip of the square-shaped rod lens.

4. The laser therapeutic device according to claim 1, wherein
the optical fiber is a quadrangular optical fiber having a quadrangular cross section, and the optical guide element is a square tube whose inner surface is a reflective surface.

5. The laser therapeutic device according to claim 1, wherein
the optical guide element has a square cross section,
the clearances are ship-bottom shaped and formed at four locations around the optical guide element, and
the imaging means and the illumination means are dispersedly arranged in the ship-bottom shaped clearances without leaving any of the ship-bottom shaped clearances unutilized.

6. The laser therapeutic device according to claim 1, wherein
the illumination means is structured by a white-color LED unit and an ultraviolet LED unit.

7. The laser therapeutic device according to claim 1, wherein
the imaging means is structured by a camera unit using a CCD image sensor.

8. The laser therapeutic device according to claim 2, wherein
the optical guide element has a square cross section,
the clearances are ship-bottom shaped and formed at four locations around the optical guide element, and
the imaging means and the illumination means are dispersedly arranged in the ship-bottom shaped clearances without leaving any of the ship-bottom shaped clearances unutilized.

9. The laser therapeutic device according to claim 3, wherein
the optical guide element has a square cross section,
the clearances are ship-bottom shaped and formed at four locations around the optical guide element, and
the imaging means and the illumination means are dispersedly arranged in the ship-bottom shaped clearances without leaving any of the ship-bottom shaped clearances unutilized.

10. The laser therapeutic device according to claim 4, wherein
the optical guide element has a square cross section,
the clearances are ship-bottom shaped and formed at four locations around the optical guide element, and
the imaging means and the illumination means are dispersedly arranged in the ship-bottom shaped clearances without leaving any of the ship-bottom shaped clearances unutilized.

11. The laser therapeutic device according to claim 2, wherein
the illumination means is structured by a white-color LED unit and an ultraviolet LED unit.

12. The laser therapeutic device according to claim 3, wherein
the illumination means is structured by a white-color LED unit and an ultraviolet LED unit.

13. The laser therapeutic device according to claim 4, wherein
the illumination means is structured by a white-color LED unit and an ultraviolet LED unit.

14. The laser therapeutic device according to claim 5, wherein
the illumination means is structured by a white-color LED unit and an ultraviolet LED unit.

15. The laser therapeutic device according to claim 8, wherein
the illumination means is structured by a white-color LED unit and an ultraviolet LED unit.

16. The laser therapeutic device according to claim 2, wherein
the imaging means is structured by a camera unit using a CCD image sensor.

17. The laser therapeutic device according to claim 3, wherein
the imaging means is structured by a camera unit using a CCD image sensor.

18. The laser therapeutic device according to claim 4, wherein
the imaging means is structured by a camera unit using a CCD image sensor.

* * * * *